(12) United States Patent
Gatewood, Jr. et al.

(10) Patent No.: US 6,411,450 B1
(45) Date of Patent: Jun. 25, 2002

(54) METHOD OF ASSESSING THE EFFECTIVENESS OF A LASER EYE PROTECTION DEVICE

(75) Inventors: Walter P. Gatewood, Jr.; Jerri A. Tribble, both of Lexington Park; James B. Sheehy, Leonardtown, all of MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/947,633

(22) Filed: Sep. 7, 2001

(51) Int. Cl.[7] ................................................. G02B 5/22
(52) U.S. Cl. ........................................................ 359/885
(58) Field of Search ........................... 351/44, 41, 177, 351/200, 246, 159; 359/885, 891

(56) References Cited

U.S. PATENT DOCUMENTS 5,116,113 A * 5/1992 Chu ........................... 351/163

* cited by examiner

*Primary Examiner*—Hung Xuan Dang
(74) *Attorney, Agent, or Firm*—Ron Billi

(57) ABSTRACT

A method of assessing the effectiveness of a laser eye protection (LEP) device having an interference filter surface (IFS) includes (A) specifying optical densities at a number of points on the IFS for a user specified range of incident angles of a given wavelength of laser light at each of the number of points; (B) entering the specified optical densities into a computer; (C) entering properties of the IFS into the computer; (D) entering properties of an eye into the computer; (E) entering properties of the given wavelength of laser radiation into the computer; (F) defining a grid for the IFS and assigning values of optical densities to points on the IFS grid using the optical densities from step (A) and interpolation; (G) assigning different colors to different optical densities, respectively; (H) generating and displaying a three-dimensional image of the eye and IFS using a graphical user interface (GUI); (I) using the GUI, selecting an incident angle orientation for the given wavelength of laser light and coloring the IFS as a function of optical density on the IFS; (J) using the GUI, selecting an eye orientation and projecting a pupil surface onto the IFS at a point of interest along the incident angle selected in step (I); and (K) determining an average optical density for that portion of the IFS intersected by the projected pupil surface of step (J) and coloring the portion in accordance with the determined average optical density.

16 Claims, 6 Drawing Sheets

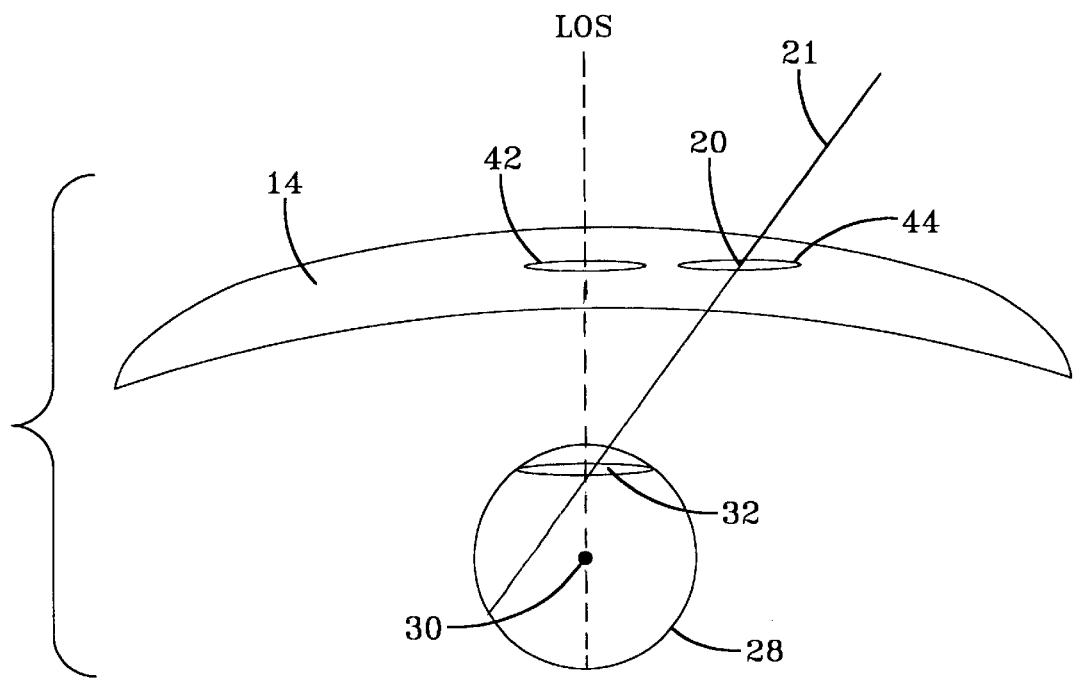
FIG-8
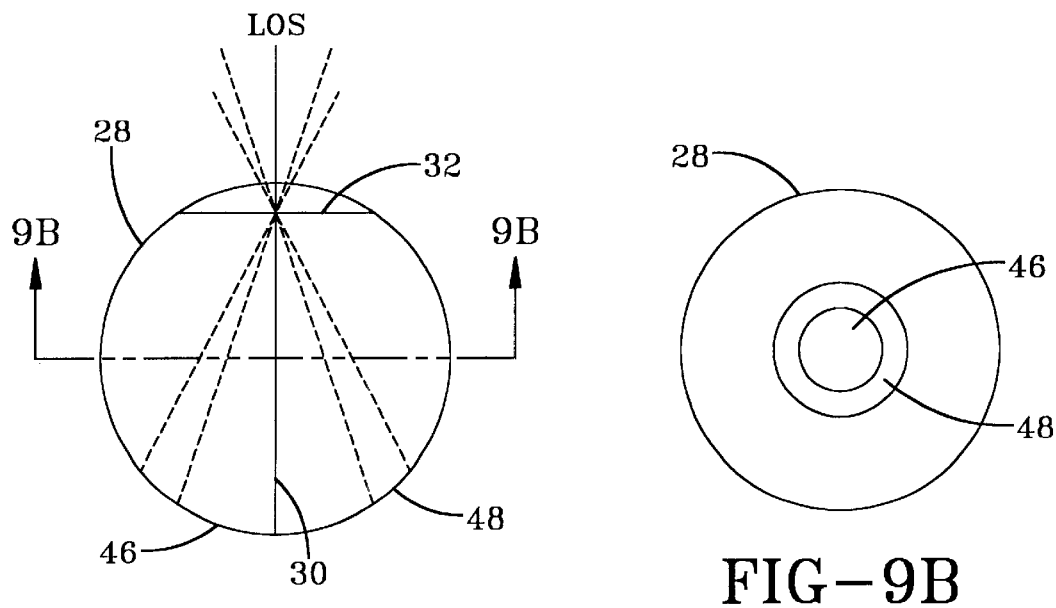
FIG-9A
FIG-9B

METHOD OF ASSESSING THE EFFECTIVENESS OF A LASER EYE PROTECTION DEVICE

STATEMENT OF GOVERNMENT INTEREST

The invention described herein may used by or for the Government of the United States of America without the payment of any royalties therefor.

REFERENCE TO COMPUTER PROGRAM LISTING APPENDIX

A Computer Program Listing Appendix is hereby expressly incorporated by reference. The Computer Program Listing Appendix includes two duplicate compact discs. The files on each compact disc, their size in bytes, and the date created are:

BACKGROUND OF THE INVENTION

The invention is a software based model for the design and assessment of laser eye protection and in particular interference filter type laser eye protection.

Interference based filter technology has been under development in all branches of the Department of Defense since the 1980s. By creating square or sinusoidal gratings in a material layer through either controlled exposure to mutually interfering laser beams in appropriate photographic media or by depositing multiple layers of material with alternating refractive indices, light rays whose wavelength is the same as the path length between the refractive interfaces are preferentially reflected rather than transmitted.

There are basically three different manufacturing processes under development to produce the requisite interference layers to provide adequate laser eye protection. All three technologies reject narrow "notches" of the spectrum

| File Name | Size | Date Created | |
|---|---|---|---|
| A LEP | 1,281 | 07-03-00 11:51 a | a.lep |
| AGVIEWER C | 13,459 | 07-03-00 11:51 a | agviewer.c |
| AGVIEWER H | 3,642 | 07-03-00 11:51 a | agviewer.h |
| ANASAL LEP | 1,284 | 07-03-00 11:51 a | aNasal.lep |
| ATEMP~14 LEP | 1,283 | 07-03-00 11:51 a | aTemporal.lep |
| B LEP | 1,281 | 07-03-00 11:51 a | b.lep |
| C LEP | 1,304 | 07-03-00 11:51 a | c.lep |
| DEFAULT DAT | 12,788 | 07-03-00 11:51 a | default.dat |
| DEFAULT LEP | 1,281 | 07-03-00 11:51 a | default.lep |
| DEMO CPP | 104,107 | 08-10-00 4:04 p | demo.cpp |
| DEMO TCL | 32,104 | 08-10-00 4:04 p | demo.tcl |
| DWBOG~28 C | 1,922,441 | 07-03-00 11:51 a | DwbOglmodel.c |
| DWBOG~30 H | 2,725 | 07-03-00 11:51 a | DwbOglmodel.h |
| DWBTOOGL H | 403 | 07-03-00 1:20 p | dwbtoogl.h |
| GENER~34 | 48 | 07-03-00 11:51 a | GENERATE_CODE |
| GLUTDEFS | 1,155 | 07-03-00 11:51 a | glutdefs |
| IMAGE H | 222 | 07-03-00 11:51 a | image.h |
| INFO TCL | 9,131 | 07-03-00 11:51 a | info.tcl |
| INFO1 TCL | 8,441 | 07-03-00 11:51 a | info1.tcl |
| INFO2 TCL | 3,179 | 07-03-00 11:51 a | info2.tcl |
| INTER~46 CPP | 10,912 | 07-03-00 11:51 a | interpolation.cpp |
| INTER~48 H | 1,723 | 07-03-00 11:51 a | interpolation.h |
| LIMIT~50 TCL | 4,065 | 07-03-00 11:51 a | limitedFloatSpinner.tcl |
| MAKEFILE | 1,608 | 07-03-00 11:51 a | Makefile |
| MATRIX3D C | 18,500 | 07-03-00 11:51 a | matrix3d.c |
| MATRIX3D H | 2,770 | 07-03-00 11:51 a | matrix3d.h |
| MODEL DWB | 324,946 | 07-03-00 11:51 a | model.dwb |
| MODEL~60 VAR | 2,600 | 07-03-00 11:52 a | model.vars |
| MULTI~62 TCL | 2,521 | 07-03-00 11:51 a | multipleLimitedFloatDialog.tcl |
| OD_BAD DAT | 16,854 | 07-03-00 11:51 a | od_bad.dat |
| OD_GOOD DAT | 12,788 | 07-03-00 11:51 a | od_good.dat |
| PIC1 BMP | 30,056 | 07-03-00 11:51 a | pic1.bmp |
| PRECI~70 H | 68 | 07-03-00 11:51 a | precision.h |
| SURFACE DWB | 37,069 | 07-03-00 11:51 a | surface.dwb |
| TKFONT H | 6,932 | 07-03-00 11:51 a | tkFont.h |
| TKINT~76 H | 26,402 | 07-03-00 11:51 a | tkInt4.0.h |
| TKINT~78 H | 29,681 | 07-03-00 11:51 a | tkInt4.1.h |
| TKINT~80 H | 31,083 | 07-03-00 11:51 a | tkInt4.2.h |
| TKINT~82 H | 36,523 | 07-03-00 11:51 a | tkInt8.0.h |
| TKINT~84 H | 36,416 | 07-03-00 11:51 a | tkInt8.0p2.h |
| TKPORT H | 717 | 07-03-00 11:51 a | tkPort.h |
| TKWIN H | 1,426 | 07-03-00 11:51 a | tkWin.h |
| TKWININT H | 5,606 | 07-03-00 11:51 a | tkWinInt.h |
| TKWIN~92 H | 2,829 | 07-03-00 11:51 a | tkWinPort.h |
| TOGL C | 93,137 | 07-03-00 11:51 a | togl.c |
| TOGL H | 7,436 | 07-03-00 11:51 a | togl.h |
| VFN H | 3,079 | 07-03-00 1:13 p | vfn.h |
| XVIRIS H | 1,870 | 07-03-00 1:13 p | xviris.h |
| 48 files | 2,871,176 bytes | | | by design. The peak wavelength rejected (i.e. the exact spectral location) is dependent upon the fringe spacing and incident angle of the impinging radiation with respect to the fringe gradient (i.e. the direction perpendicular to the plane of refractive index fringes at any location). This requires that the filter be carefully designed to reject anticipated incident wavelengths at angles determined by the relative location of the eye behind the laser eye protection (LEP) surface over the range of possible incidence angles.

Prior to the present invention, the inventors were aware of only one other attempt at a similar effort to overlay either predicted or measured angular rejection performance with precise geometric rejection requirements for any eye of a given description and location behind the LEP surface. That effort was solely designed to describe holographic visors and model their predicted performance against eye requirements in Visual Basic.

SUMMARY OF THE INVENTION

The primary object of the present invention is to provide an accurate, data-based, three-dimensional representation (graphical) of the protection provided by reflective (i.e., dielectric stacks, holograms, or rugates) or hybrid filters (combination of interference technologies or interference filters and absorptive dyes). The preferred embodiment focuses on modeling the Navy's hybrid spectacles and visors. However, the novel aspects and advantages described herein are applicable to any reflective filter or barrier material.

One aspect of the invention is to assess the effectiveness of an existing LEP device, such as a visor or a pair of spectacles. Another aspect of the invention is to develop, evaluate, or modify a proposed filter design.

The present invention generates a graphical three-dimensional representation in real time of the complex geometry of interference filters. The three-dimensional graphic and assessment features permit the user to completely model the protection for any desired choice or combination of eye parameters or incident laser direction. The invention displays protection based on the actual optical density recorded across a number of locations on an actual filter surface over a range of incident angles. These features are combined with real time response to user inputs through a graphical user interface (GUI) resulting in a powerful new tool for assessing the degree of protection provided by interference based laser eye protection.

The risk assessment features of the invention allow the user to quickly see which portions of the interference filter fail to protect the retina and more specifically the user defined areas around the central fovea. The ability to view which eye and laser incidence angles produce hazards in user defined regions of the retina is an important feature. With this feature, the user can weigh the likelihood of injury against other important aspects of the filter such as overall transmittance (i.e. visibility through the LEP device) or transmittance of key phosphors or displays.

The invention provides a method of assessing the effectiveness of a laser eye protection (LEP) device having an interference filter surface (IFS), comprising (A) specifying optical densities at a number of points on the IFS for a user specified range of incident angles of a given wavelength of laser light at each of the number of points; (B) entering the specified optical densities into a computer; (C) entering properties of the IFS into the computer; (D) entering properties of an eye into the computer; (E) entering properties of the given wavelength of laser radiation into points on the computer; (F) defining a grid using for the IFS and assigning values of optical densities to points to different optical densities, respectively; (H) generating and displaying a three-dimensional image of the eye and IFS using a graphical user interface (GUI), (I) using the GUI, selecting an incident angle orientation for the given wavelength of laser light and coloring the IFS as a function of optical density on the IFS; (J) using the GUI, selecting an eye orientation and projecting a pupil surface onto the IFS at a point of interest along the incident angle selected in step (I); and (K) determining an average optical density for that portion of the IFS intersected by the projected pupil surface of step (J) and coloring the portion in accordance with the determined average optical density.

In one aspect of the invention, the specified optical densities of step (A) are obtained by providing an LEP device, exposing the LEP device to the given laser wavelength and measuring optical densities at the number of points on the IFS for the user specified range of incident angles at each of the number of points.

In one embodiment, the IFS has a spherical shape and the properties in step (C) include a radius of curvature, a face form angle, a pantoscopic tilt, a substrate transparency, and a location of an optical center of the IFS; and the properties in step (D) include an eye location, a pupil diameter and an amount of eye rotation.

In another embodiment, the IFS has a toroidal shape and the properties in step (C) include two radii of curvature, a pantoscopic tilt, a substrate transparency, and a location of an optical center of the IFS; and the properties in step (D) include an eye location, a pupil diameter, an amount of eye rotation and an interpupillary distance.

The invention further includes, (L) selecting a second grid on the IFS, and, for each grid point on the second grid and for eye orientations generated by rotating the eye, projecting a pupil surface onto the IFS at said each grid point and calculating the maximum incident angle at which the given wavelength of laser light may enter the pupil at said each grid point; and displaying in tabular form the location of said each grid point and its respective maximum incident angle.

In one embodiment, the IFS has a spherical shape and the calculating in step (L) is limited such that the maximum incident angle at which the given wavelength of laser light may enter the pupil at said each grid point is found in a plane defined by an eye center point, a center of curvature of the IFS and each grid point, respectively.

Another aspect of the invention is, (M) selecting a grid point and its maximum incident angle from step (L) and displaying on the GUI a three-dimensional image of the eye and incidence angles of laser radiation corresponding to the maximum incident angle for that grid point. The invention further comprises displaying numerically the eye orientation and laser light incident angle orientation corresponding to the maximum incident angle for that grid point.

Yet another feature of the invention is, (N) using the GUI, selecting a single maximum incident angle for the given wavelength of laser light for all grid points and coloring the IFS as a function of optical density on the IFS.

The invention further includes, (O) for the eye and incidence angles of laser radiation from step (M), displaying on the GUI a three-dimensional image of only those eye and laser light incident angle orientations that will result in laser light striking the fovea critical region or the fovea caution region.

Still another aspect of the invention is, (P) for the eye and incident angles of laser radiation from step (M), displaying on the GUI a three-dimensional image of the eye and IFS wherein the IFS is colored with a first color at points where the laser light will strike the fovea critical region, a second color where the laser light will strike the fovea caution region and a third color where the laser light will strike neither the fovea critical region or the fovea caution region.

Further objects, features and advantages of the invention will become apparent from the detailed description in conjunction with the following drawings.

BRIEF DESCRIPTION OF THE DRAWING

FIG. 8 is a perspective side view of a three-dimensional display according to the invention.

FIGS. 9A and 9B show how the fovea regions are defined.

DETAILED DESCRIPTION OF THE PREFERRED EMBODIMENTS

The present invention is a software-based design and analysis tool that displays the degree of angular coverage provided by interference based laser eye protection. The software is loaded into a computer. Inputs relevant to the LEP model are entered via a keyboard or disk drive while status, parameters, and results are displayed on a monitor. Any display of interest may be printed.

The results of the model are presented in two formats. First, there is a graphical representation of the interference filter surface (with a selectable frame/lens overlay) and the eye. The graphical 3-dimensionsal image can be turned to view it from any perspective and from any distance. Additionally, clipping planes may be used so that only one slice of the graphic is displayed. The interference filter surface is painted with a color scheme, for example, a green to red color scheme, to denote the level of protection (protection levels are user defined). The results can also be displayed in tabular form. The computer program operates and produces results in real time based on geometry and on performance data for actual interference filters. The graphical and tabular displays are described in detail below.

Figure 1:
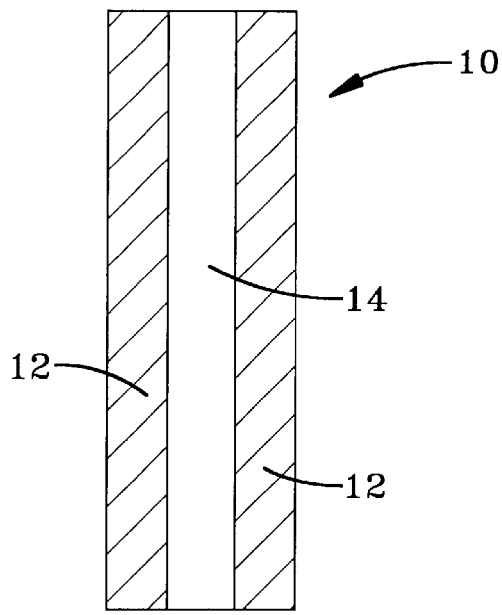
FIG. 1 is a schematic cross-section of a portion of a lens of a LEP device.

FIG. 1 is a schematic cross-section of a portion of a lens 10 of an LEP device. The lens 10 includes an interference filter surface (IFS) 14 sandwiched between a cap and substrate or base 12. Methods of manufacturing the lens 10 are well known and will not be discussed further.

Figures 2A, 2B:
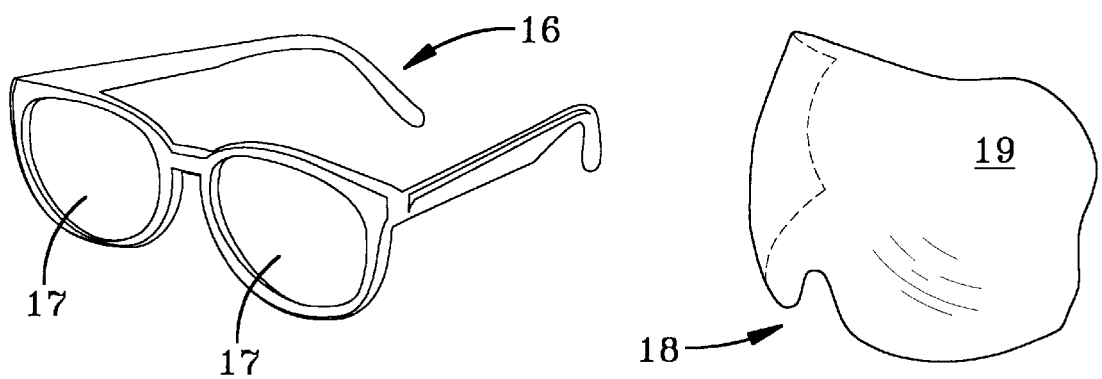
FIGS. 2(A) and (B) show two examples of LEP devices.

FIGS. 2(A) and (B) show two examples of LEP devices. FIG. 2(A) shows a pair of spectacles 16 wherein the lenses 17 comprise an IFS embedded between a cap and base. The lenses 17 and the IFS embedded therein typically have a spherical shape defined by a radius of curvature. FIG. 2(B) shows a visor 18 wherein the visor shield 19 comprises an IFS embedded between a cap and base. The visor shield 19 and the IFS embedded therein typically have a toroidal shape defined by two radii of curvature. FIGS. 2(A) and (B) are merely exemplary. A variety of devices may incorporate laser eye protection using an IFS embedded between a cap and base.

The rejection performance of the IFS 14 is particular to the wavelength of the anticipated incident laser. That is, the invention determines protection based on geometry selected by user specified eye and lens parameters and dependent on user supplied data representing the actual or desired angular transmission performance at the user's desired laser wavelength. Thus, the laser wavelength is understood by the user and is not explicitly used in the computer software. The user supplies angular transmission performance to the software in the form of a table of optical density as a function of incidence angle per surface location on the IFS 14.

In the design aspect of the invention, the optical densities are specified based on the desired optical density for the LEP device being designed. In another aspect of the invention, where existing LEP devices are being evaluated, the filter is exposed to the design laser wavelength. Then, for each point on the IFS, the optical density (i.e. the negative logarithm of transmittance) is measured over the range of incident angles relevant to eye protection (may be determined within the software).

Table 1 is an example of how the measurement parameters and optical densities (whether design values or measured values) might be presented for a holographic filter with a spherical interference structure.

TABLE 1

|  | R = 0 | R = 2 | R = 4 | R = 6 | R = 8, . . . |
|---|---|---|---|---|---|
| −50° | 0.5 | 0.5 | 0.3 | 0.3 | 0.2 |
| −49° | 1.1 | 1.1 | 0.9 | 0.9 | 0.8 |
| −48° | 2.1 | 2.1 | 1.9 | 1.9 | 1.8 |
| −47° | 3.1 | 3.1 | 2.9 | 2.9 | 2.8 |
| . . . | 4.7 | 4.7 | 4.5 | 4.5 | 4.4 |
| +47° | 3.1 | 3.1 | 2.9 | 2.9 | 2.8 |
| +48° | 2.1 | 2.1 | 1.9 | 1.9 | 1.8 |
| +49° | 1.1 | 1.1 | 0.9 | 0.9 | 0.8 |
| +50° | 0.5 | 0.5 | 0.3 | 0.3 | 0.2 |

The first row of Table 1 indicates the distance in millimeters from the holographic center. Thus, R=0 is the holographic center while R=2 is a circle of points two mm from the holographic center. In the case of a spherical IFS, the LEP properties are symmetrical about the holographic center. Thus, it is only necessary to specify optical density per incident angle at one location per radial distance from the holographic center. In the example above, the last radial value shown is R=8, however, the radial measurements may extend as far as necessary. Furthermore, increments of two millimeters and one degree are shown by way of example only. Other increments may be used depending on the application.

It is noted that in the case of a non-spherical IFS, where radial symmetry is not applicable, the number of points on the IFS will be greater (multiple locations per radius will be required). Furthermore, depending on the design of the fringe structure, the optical density may not be symmetric about the surface normal and may thus require optical densities to be specified as a function of two angles away from the surface normal at each surface location (i.e., a 4 dimensional table of performance may be required).

Figure 3:
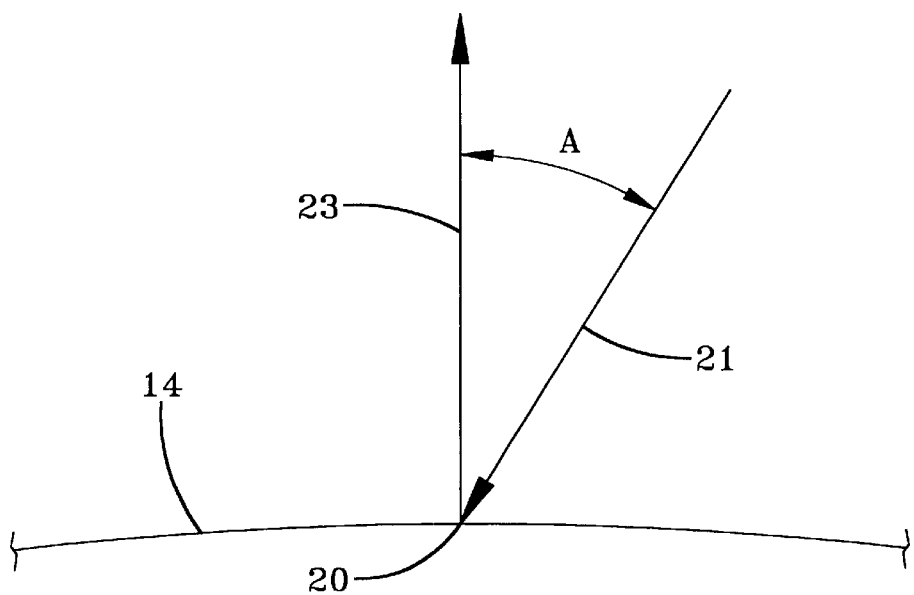
FIG. 3 shows the definition of the incident angle for an incident light ray.

The first column in Table 1 indicates the laser incidence angle. As shown, the angle varies from −50° to +50° in one degree increments. Other ranges and increments may be used as needed. As shown in FIG. 3, the incident angle A of the light ray 21 is the angle between incident ray 21 and the surface normal 23 at a point of interest 20 on the IFS 14. The individual cells of Table 1 are the design or measured values (depending on user application) of the optical density for a particular point of interest 20 on the IFS 14 that is subjected to a particular incident angle A. In this example, the radial position from the IFS center to the point of interest 20 is specified in the column heading and the incidence angle of the laser A is specified in the row heading.

The information in Table 1 is entered into the computer as a file. The user may specify through the graphical user interface, which data file is to be used in generating the graphical display of protection performance. The invention uses interpolation to compute optical densities for points of interest not specified in Table 1. The interpolation method may be, for example, bilinear or biquadratic.

Properties of the IFS 14, the eye and incident rays are also entered into the computer through the GUI. In the case where the LEP is a pair of spectacles and the IFS has a spherical shape, the properties of the IFS include the radius of curvature, face form angle, pantoscopic tilt, and location of the optical center of the IFS. In the case where the LEP is a visor and the IFS has a toroidal shape, the properties of the IFS include the two radii of curvature, the pantoscopic tilt, and the location of the optical center of the IFS (if the fringe structure has a center of symmetry).

The properties of the eye include location (pupillary distance and eye relief), the pupil diameter and range of eye movement to be considered. In an exemplary embodiment, the pupil diameter is 8 mm and the range of eye movement is 35° in any direction. In the case where the IFS is toroidal in shape, such as a visor, it is also necessary to include the interpupillary distance and vertical interpupillary separation.

Figure 4:
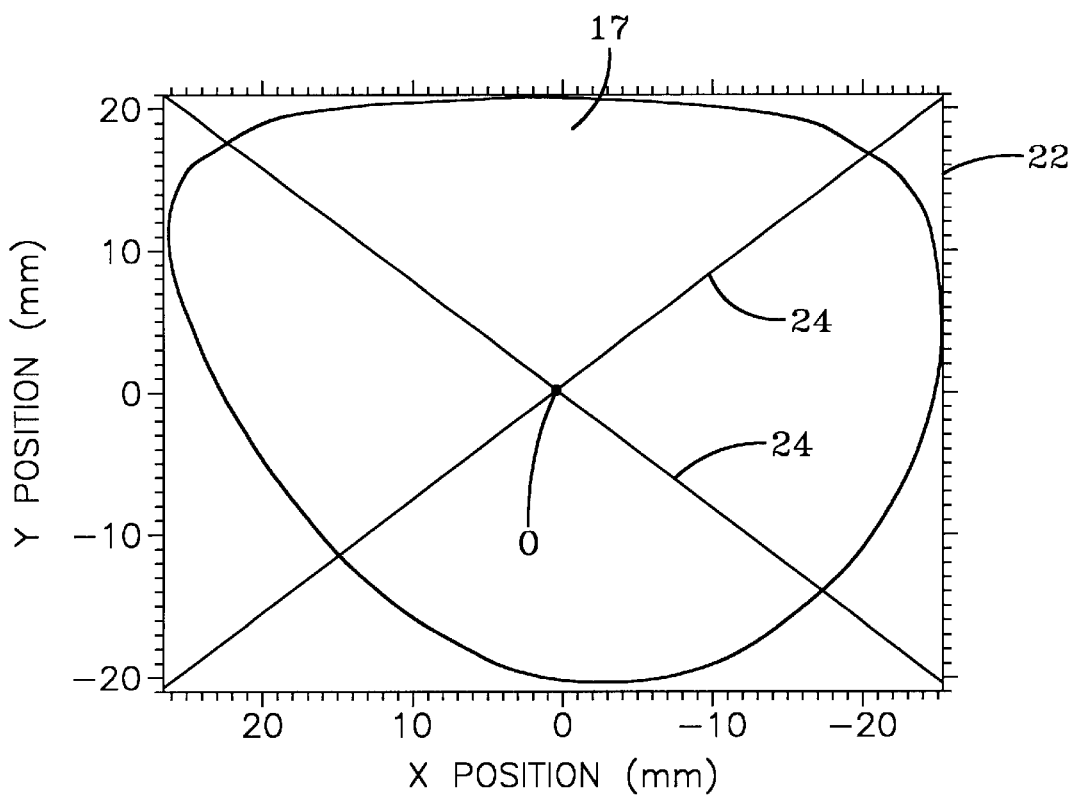
FIG. 4 shows how the origin O of an exemplary coordinate system is determined.

FIG. 4 shows how the origin O of an exemplary coordinate system is determined for the case of a pair of spectacles 16 having a lens 17. In a known manner, a rectangle 22 is drawn with its sides intersecting the outermost points of the lens 17. The intersection of the diagonals, 24, of the rectangle 22 is the "½ab" point for the lens 17 and, in a preferred embodiment, is used as the origin O of a Cartesian coordinate system. Other coordinate systems with different origins and orientations could be used.

Figure 5:
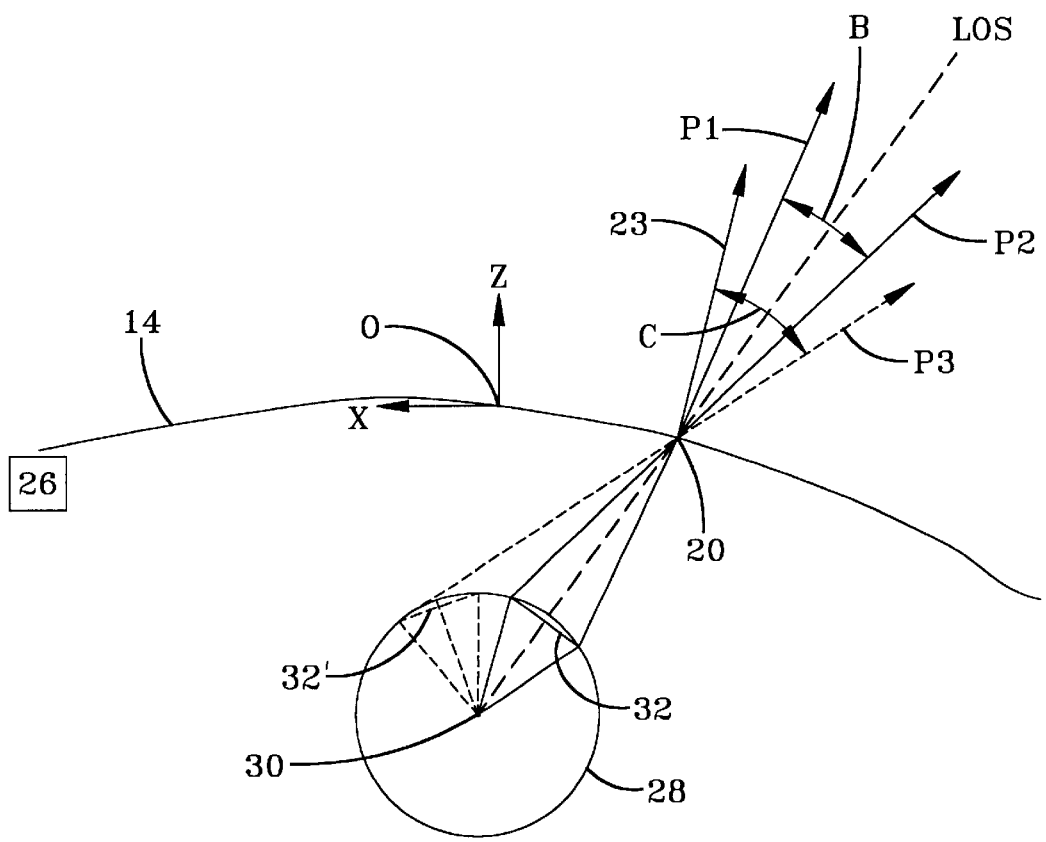
FIG. 5 schematically depicts objects, lines, and angles used in the invention.

FIG. 5 schematically shows an example of a coordinate system used in the invention. The origin O is as described in FIG. 4. FIG. 5 represents a lens 17 of a pair of spectacles 16 having a spherically shaped IFS 14. The nose 26 of the wearer is shown to clarify the orientation in the example drawn in FIG. 5. The "½ab" point of the exemplary lens 17 is designated as the origin O of a rectangular coordinate system having axes x, y and z. The y axis is perpendicular to the plane of the figure.

From the origin O all other locations may be specified by their distance (in mm, for example) along the x, y and z axes, where the positive x-direction points towards the nose and the positive z-direction points straight ahead from the wearer. The IFS 14 may be tilted about two orthogonal axes representing face form angle (tilt in the horizontal plane) and pantoscopic tilt (tilt in the vertical plane). The location of the points on the IFS is corrected for these tilts using standard matrix algebra. While the refractive power of the eye lens, cornea and aqueous are not presently considered, it is possible to do so by applying known formulas.

An eye 28 has its center 30 located at an x, y and z offset from the origin O. The holographic center of the IFS 14 will, in general, not coincide with the "½ab" point used as the origin O. Thus, the location of the holographic center (not shown) may also be defined by an x, y and z offset from the origin O. A point of interest 20 on the IFS 14 is defined by x and y coordinates. The z coordinate for a point of interest 20 on the IFS may be computed from the mathematical expression for the shape of the IFS and the other known geometric parameters. Thus, the computer program can determine the z coordinate mathematically. The line perpendicular to the IFS 14 at the point of interest 20 is the surface normal 23.

Damage to the eye 28 occurs when laser radiation of a sufficient intensity enters the eye through the pupil and strikes the retina. Thus, the focus of the invention is on laser energy that can enter the pupil. The pupil comprises a circle of points equidistant from the center of the eye, having a specified diameter (user specified). The pupil 32 of the eye 28 in FIG. 5 is shown in a first position and in a second position (32') rotated from the first position. As discussed previously, both pupil size and the amount of eye rotation in degrees (i.e. the range of eye movement considered) are input parameters of the method.

To understand the steps performed by the invention consider first, the angle of incidence that the IFS must reject at point 20 if the eye 28 is turned so that the line of sight LOS goes directly through this point 20. Lines P1 and P2 extending from pupil 32 through point of interest 20 define the extreme rays which can enter the pupil 32 through point 20. If, for example, the IFS rejected all rays incident from the surface normal out to ray P2, then the pupil as oriented here, would be entirely protected. However, the eye 28 may also rotate. Pupil 32' represents the location of the pupil 32 after the eye rotates to a user specified range limit. Line P3 extending from pupil 32' through point of interest 20 defines an additional angle through which a ray may enter pupil 32 through point of interest 20. Therefore, "C" defines the greatest incidence angle through which a ray may enter pupil 32 through point of interest 20 as the eye 28 rotates through the defined eye movement.

The geometric orientation of the laser is chosen by specifying an "incident angle azimuth" and "incident angle elevation." Azimuth is the angle of rotation about the y-axis with 0 degrees defined at the z-axis and positive away from the nose. Elevation is the angle of rotation about the x-axis with 0 degrees defined at the z-axis and positive upward.

Figure 6:
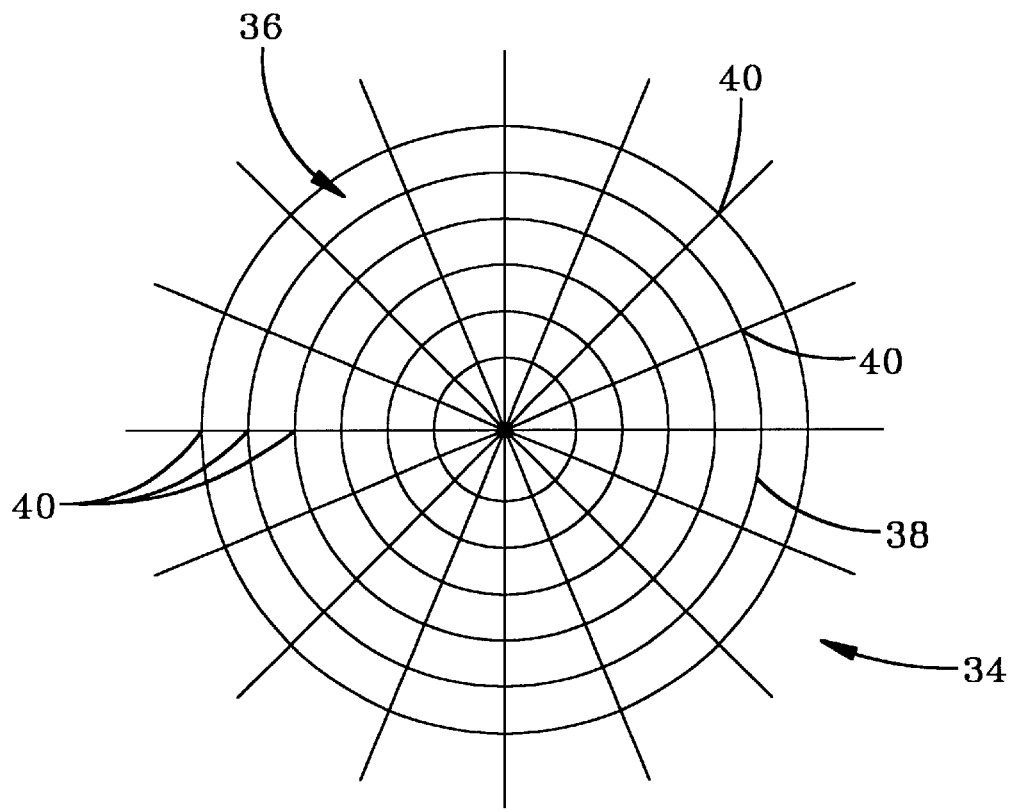
FIG. 6 is a top view of a grid used to generate an image of an interference filter surface.

The computer generates and displays a three-dimensional image of the eye 28 and IFS 14 using a graphical user interface (GUI). An exemplary color scheme shown in FIG. 7 varies from red, signifying undesirable leakage, to green, signifying desirable "blockage". FIG. 6 is a top view of a grid used to generate an image of an IFS 14. As shown in FIG. 6, the IFS 14 is generated by specifying a grid 34. The resolution of the grid 34 may be varied by varying the number of "pie" slices 36 and the number of concentric circles 38. Points 40 of grid 34 are the points of intersection between the "pie" slices 36 and the concentric circles 38. For each point 40 on the grid 34, the color scheme is applied in the following manner.

Figure 7:
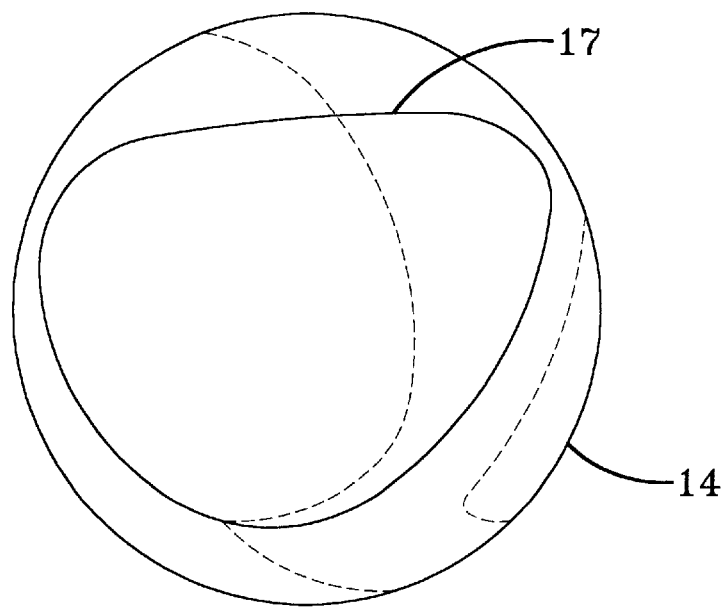
FIG. 7 is a top view of a three-dimensional display of an interference filter surface.

For each point 40 on grid 34, the angle between the surface normal at that point and ray 21 (incident at the user specified azimuth and elevation) is calculated. This angle is the incident angle A referred to in FIG. 3. Then, using the data from Table 1 and an interpolation method (of appropriate dimensionality), the optical density for each point 40 is determined. Optical density is then mapped for each point 40 to a color value, using the color scheme discussed above. A shading routine is used to color the areas between the points. FIG. 7 is an example of a top view of an IFS 14 generated using a grid 34. The grid lines are not shown. If desired, the outline of lens 17 (See FIGS. 2A and 4) may be overlaid on the IFS 14. The dotted lines in FIG. 7 represent borders between areas of different color, and, hence, different optical density.

The above computation produces a color-coded visual representation of the efficiency of the IFS 14 in blocking the incident rays (parallel to ray 21 for example). To view the efficiency of the IFS 14 in blocking a ray having another geometric orientation, the user may simply change the values of "incident angle azimuth" and "incident angle elevation". In addition to displaying a visual three-dimensional image of the eye and IFS, the GUI numerically displays the various geometric and other input parameters for the eye, pupil, IFS and incident ray choice. These parameters may be varied on the GUI to view a variety of scenarios.

In addition to the color representation of whole lens performance for a user specified incident laser azimuth and elevation, the graphic display includes a projection of the pupil 32 onto the IFS 14 in the direction of the user specified incident laser (from the pupil center 33 towards the IFS 14 parallel to ray 21, for example). The eye's orientation must be known in order to determine the pupil center 33. Eye orientation is specified by selecting an "eye azimuth" and "eye elevation." Azimuth is the angle of rotation about the y-axis with O defined at the z-axis. Elevation is the angle of rotation about the x-axis with O defined at the z-axis.

The optical density of the area of the IFS 14 within the outline of the pupil projection is a logarithmic average. Using this average optical density, that area is colored in accordance with the optical density color scheme. This visual display allows the user to focus on particular portions of the IFS 14 through which a ray may actually enter the pupil 32. FIG. 8 is a perspective side view of the display just described. Eye 28 with pupil 32 is shown in user selected geometric relation to the IFS 14. The projection of the pupil 32 along the line of sight LOS is outlined at 42 on the IFS. The projection of the pupil 32 along the user specified direction of ray 21 is outlined at 44. For purposes of clarity, the borders between regions of different color (i.e., different optical density) are not shown in FIG. 8. The color of the area within pupil outline 44 represents the mathematical average of the optical density in that area, for the critical ray 21.

Another feature of the inventive method is the "Maximum Threat Table" (MTT). Here, the term "threat" refers to incident laser angles which threaten the retina and may be considered synonymous with "hazard". First, the user specifies a second grid spacing for the IFS 14. The second grid, in this embodiment, uses rectangular geometry (considered easier from the user's point of view) but could also use the polar geometry described above. For a given point of interest on the second grid spacing of the IFS 14, the method determines the maximum angle from the surface normal to any and all rays that can enter the eye (including eye movement out to the user specified limit, see also FIG. 3). The MTT will, therefore, show a maximum angle for each point on the selected grid spacing. The MTT is particularly useful as a design tool.

In the case where the IFS has a spherical shape, generating the MTT is made simpler by incorporating a limiting assumption that for a given point of interest 20 on the IFS, the maximum incidence angle at which a ray may enter the eye is found in or reasonably near the plane containing the point of interest 20, the eye's center 30, and the center of curvature of the spherical IFS. This assumption reduces a three-dimensional iteration to a one-dimensional iteration to find the maximum angle (in one plane).

Further features of the invention allow the user to quickly identify the laser/eye scenarios that are most hazardous to the retina. In these features of the invention, the primary concern is to alert the user to leakage nearest to the central fovea (the region closest to the visual axis) and thereby determine whether the eye protection is adequate. To accomplish this task, the invention uses the "Max Threat Angle" (MTA), "Max Critical Threat Angle" (MCTA) and "Color Lens with Max Criticality" (CLMC) features.

A "fovea critical region" and a "fovea caution region" are user defined. The fovea critical region is a circular region around the visual axis and is defined by an angle as follows. As shown in FIG. 9A, the point of intersection of the line of sight (LOS) with the rear of the eye 28, for any position of the eye 28, is assumed to be the visual axis. The LOS is pivoted about its intersection with the pupil 32, as shown by the dotted lines, to generate a circular surface 46 on the rear of the eye 28. FIG. 9B is a sectional view taken along the line 9B—9B of FIG. 9A. The angle through which the LOS is pivoted defines the fovea critical region 46. The fovea caution region 48 is an annular region around the fovea critical region 46. The fovea caution region 48 is defined by an angle in a manner similar to the fovea critical region 46. Thus, the defining angle for the fovea caution region 48 will always be greater than the defining angle for the fovea critical region 46. However, the actual fovea caution region is the annular area defined by the difference between the fovea caution angle and the fovea critical angle.

The visual display of "Max Threat Angle" (MTA) is a three-dimensional image of the eye 28 and incident laser orientations that resulted in the maximum incident angle for a given point (e.g. point 20) on the IFS. For instance, after generating the MTT using, for example, a 5 mm grid, assume the maximum angular requirement at a given location (e.g., x=5 mm, y=5 mm) to be 27 degrees. The user can then open the MTA menu and enter 5 for both the x and y values of the "point of interest" 20 to view the eye and incident ray orientations that gave rise to the 27 degree requirement. These eye and incident ray orientations may also be displayed in tabular form.

The eye and laser orientations of the MTA can be further refined using the "Max Critical Threat Angle" (MCTA) function. The user selects values for the fovea critical and caution angles. MCTA will display only the eye and critical orientations of the MTA that result in a ray striking either the fovea critical or caution regions. These eye and critical ray orientations may be displayed in tabular form or as a three-dimensional image.

The "Color Lens with Max Criticality" (CLMC) function uses the eye and critical ray orientations from the MCTA function. The CLMC displays on the GUI a three-dimensional image of the eye and IFS where the IFS is colored with one color at points where the laser light will strike the fovea critical region, a second color where the laser light will strike the fovea caution region, and a third color where the laser light will strike neither the fovea critical region or the fovea caution region.

The user can selectively adjust the fovea critical angle or the fovea caution angle in the CLMC function to observe which IFS locations allow transmission within the fovea critical or fovea caution regions. In this way, the invention directly shows where a given filter design is failing to protect the regions closest to the foveal and parafoveal regions.

Overview of Computer Software used with the Invention

Figure 10:
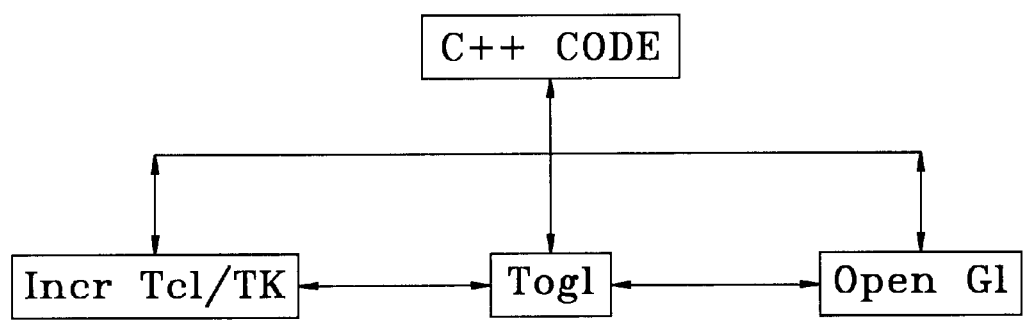
FIG. 10 schematically shows software components used with the invention.

The software used with the invention is written in C++ and Tcl/Tk languages. Tcl/Tk, enhanced by incr Tcl and incr Tk, is used for specifying the user interface. C++ is used for the underlying calculations. OpenGl, a C library is used for drawing the graphics. Togl allows OpenGl rendering in a Tk window. Designer's Workbench (DWB), 3-D modeling software made by Centric Software, Inc., was used initially for creation of the lens and eye model and created OpenGl C code for drawing the model. The software uses a lens model that is calculated dynamically within the C++ code. FIG. 10 schematically shows the software components described above.

The user interface, written in Tcl/Tk, is located in files with the extension ".tcl". They are limitedFloatSpinner.tcl, which defines a widget for displaying and changing a floating-point value; multipleLimitedFloatDialog.tcl, which defines a dialog for displaying and changing multiple floating-point values; and demo.tcl, which contains the body of the user interface with multiple calls to the multipleLimitedFloatDialog shell.

The computational part of the software is located in the files ending in ".c", ".cpp", and ".h". The files named "interpolation.cpp" and "interpolation.h" contain interpolation routines. Files "DwbOglmodel.h", "DwbOglmodel.c" contain the part of the software that was defined in DWB. The "matrix3d.h" and "matrix3d.c" files contain linear algebra functions. With the exception of "demo.cpp", all of the remaining files in this category are incidental to the other software routines in the program. "Demo.cpp" contains most of the computations.

Togl provides the linkage between the C++ program, Tcl/Tk, and OpenGl, Tcl/Tk contains the main loop which constantly monitors user input. The functions in "demo.cpp" are event-driven. After initialization, procedures in "demo.cpp" are invoked as callbacks as a result of some action taken by the user.

Initialization

Starting in main, the program immediately passes control to Tk_Main with the command line arguments and the address of the callback initialization routine, initTogl: Tk_Main(argc,argv,initTogl).

When initTogl is called it performs the initialization for the software. Tcl/Tk, Togl, and Incr Tcl/Tk are initialized. Four functions, "initGraphics", "display", "reshape", and "idle", within demo.cc are declared, as required, as callbacks to Togl.

"InitGraphics" initializes the data structures and models and initializes the graphics. "Display" will be invoked to refresh the screen. "Reshape" will be invoked when the window is resized. "Idle" will be invoked when there is nothing else to do.

Next, a number of functions are declared to Tcl/Tk, to be invoked directly from Tcl/Tk as a result of user actions. Last of all, the Tcl/Tk interpreter is instructed to take its commands defining the GUI from the "demo.tcl" file.

Tcl/Tk Interface Functions

All Tcl/Tk Interface Functions are declared in initTogl using the Togl_CreateCommand routine from Togl. The parameters to Togl_CreateCommand are a string to use in the interpreter for invoking the interface function and the address of the interface function in "demo.cpp".

All of the interface functions have the same parameter list consisting of a structure maintained by Togl, a count of the number of actual arguments, and an array of character pointers containing the actual arguments of the interface function. For further details concerning any particular interface function refer to the Computer Program Listing Appendix.

While the invention has been described with reference to certain preferred embodiments, numerous changes, alterations and modifications to the described embodiments are possible without departing from the spirit and scope of the invention as defined in the appended claims, and equivalents thereof.

What is claimed is:

1. A method of assessing the effectiveness of a laser eye protection (LEP) device having an interference filter surface (IFS), comprising:
   (A) specifying optical densities at a number of points on the IFS for a user specified range of incident angles of a given wavelength of laser light at each of the number of points;
   (B) entering the specified optical densities into a computer;
   (C) entering properties of the IFS into the computer;
   (D) entering properties of an eye into the computer;
   (E) entering properties of the given wavelength of laser radiation into the computer;
   (F) defining a grid for the IFS and assigning values of optical densities to points on the IFS grid using the optical densities from step (A) and interpolation;
   (G) assigning different colors to different optical densities, respectively;
   (H) generating and displaying a three-dimensional image of the eye and IFS using a graphical user interface (GUI);
   (I) using the GUI, selecting an incident angle orientation for the given wavelength of laser light and coloring the IFS as a function of optical density on the IFS;
   (J) using the GUI, selecting an eye orientation and projecting a pupil surface onto the IFS at a point of interest along the incident angle selected in step (I); and
   (K) determining an average optical density for that portion of the IFS intersected by the projected pupil surface of step (J) and coloring the portion in accordance with the determined average optical density.

2. The method of claim 1 wherein the specified optical densities of step (A) are obtained by providing an LEP device, exposing the LEP device to the given laser wavelength and measuring optical densities at the number of points on the IFS for the user specified range of incident angles at each of the number of points.

3. The method of claim 1 wherein the IFS is one of a hologram, rugate, dielectric stack or combination thereof.

4. The method of claim 1 wherein the IFS has a spherical shape and the properties in step (C) include a radius of curvature, a face form angle, a pantoscopic tilt, a substrate transparency, and a location of an optical center of the IFS.

5. The method of claim 1 wherein the IFS h as a toroidal shape and the properties in step (C) include two radii of curvature, a pantoscopic tilt, a substrate transparency, and a location of an optical center of the IFS.

6. The method of claim 5 wherein the properties in step (D) include an eye location, a pupil diameter, an amount of eye rotation and an interpupillary distance.

7. The method of claim 1 wherein the properties in step (D) include an eye location, a pupil diameter and an amount of eye rotation.

8. The method of claim 1 wherein the incident angle orientation in step (I) is defined by selecting an incident angle azimuth angle and an incident angle elevation angle.

9. The method of claim 1 wherein the eye's orientation in step (J) is defined by an eye azimuth angle and an eye elevation angle.

10. The method of claim 1 further comprising:
   (L) selecting a second grid on the IFS, and, for each grid point on the second grid and for eye orientations generated by rotating the eye, projecting a pupil surface onto the IFS at said each grid point and calculating the maximum incident angle at which the given wavelength of laser light may enter the pupil at said each grid point; and displaying in tabular form the location of said each grid point and its respective maximum incident angle.

11. The method of claim 10 wherein the IFS has a spherical shape an d the calculating in step (L) is limited such that the maximum incident angle at which the given wavelength of laser light may enter the pupil at said each grid point is found in a plane defined by an eye center point, a center of curvature of the IFS and each grid point, respectively.

12. The method of claim 10 further comprising:
   (M) selecting a grid point and its maximum incident angle from step (L) and displaying on the GUI a three-dimensional image of the eye and incidence angles of laser radiation corresponding to the maximum incident angle for that grid point.

13. The method of claim 12 further comprising displaying numerically the eye orientation and laser light incident angle orientation corresponding to the maximum incident angle for that grid point.

14. The method of claim 12 wherein the properties in step (D) include a location of a fovea caution region and a location of a fovea critical region, the method further comprising:

(O) for the eye and incidence angles of laser radiation from step (M), displaying on the GUI a three-dimensional image of only those eye and laser light incident angle orientations that will result in laser light striking the fovea critical region or the fovea caution region.

15. The method of claim 14 further comprising:

(P) for the eye and incident angles of laser radiation from step (M), displaying on the GUI a three-dimensional image of the eye and IFS wherein the IFS is colored with a first color at points where the laser light will strike the fovea critical region, a second color where the laser light will strike the fovea caution region and a third color where the laser light will strike neither the fovea critical region or the fovea caution region.

16. The method of claim 10 further comprising:

(N) using the GUI, selecting a single maximum incident angle for the given wavelength of laser light for all grid points and coloring the IFS as a function of optical density on the IFS.

* * * * *